United States Patent [19]

Simon

[11] Patent Number: 5,475,093

[45] Date of Patent: Dec. 12, 1995

[54] PROCESS FOR THE PREPARATION OF AZOXYCYANIDE COMPOUNDS

[75] Inventor: Werner E. J. Simon, Heilbronn, Germany

[73] Assignee: American Cyanamid Co., Wayne, N.J.

[21] Appl. No.: 419,971

[22] Filed: Apr. 7, 1995

Related U.S. Application Data

[63] Continuation of Ser. No. 291,268, Aug. 16, 1994, abandoned.

[30] Foreign Application Priority Data

Aug. 18, 1993 [EP] European Pat. Off. .............. 93113191

[51] Int. Cl.⁶ .................... C07D 317/66; C07C 291/08
[52] U.S. Cl. .................... 534/572; 534/556; 534/566; 534/567
[58] Field of Search ........................... 534/572, 556, 534/566, 567

[56] References Cited

U.S. PATENT DOCUMENTS 5,089,486  2/1992  Wood et al. .................. 534/572 X
5,273,997  12/1993  Naisby et al. ................. 514/452

FOREIGN PATENT DOCUMENTS 9412470  6/1994  WIPO ........................... 534/566

OTHER PUBLICATIONS

Zlotin et al., *Chemical Abstracts*, 114:207072 (1990).
S. G. Zlotin, et al., "New Regiospecific Synthesis of N¹-Cyano Diazene N-Oxides", IZV.AKAD.NAUK.SSR KHIM., No. 12, 1990, pp. 2821–2826.
R. Fruttero, et al., "A Directed Synthesis of Alkyl, Aryl, and Heteroaryl–ONN–Azoxycyanides", Journal Of The Chemical Society, Chemical Communications, 1984, Letchworth GB; pp. 323–324.

*Primary Examiner*—Johann Richter
*Assistant Examiner*—Fiona T. Powers
*Attorney, Agent, or Firm*—Charles F. Costello, Jr.

[57] ABSTRACT

The invention relates to a process for the preparation of azoxycyanide compounds of the general formula

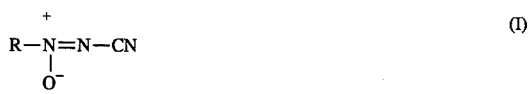

in which R represents an optionally substituted aryl or heterocyclyl group, which comprises treating a compound of the general formula

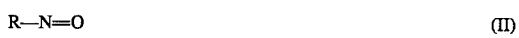

in which R is as defined above, with cyanamide or a metal salt thereof and a compound of the general formula

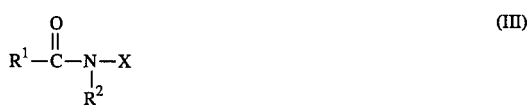

in which $R^1$ represents an optionally substituted alkyl or aryl group and $R^2$ represents a hydrogen atom or an optionally substituted alkyl or aryl group or $R^1$ and $R^2$ together represent a group

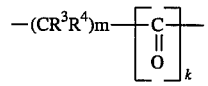

where m is 2, 3, 4 or 5, k is 0 or 1 and each of $R^3$ and $R^4$ independently represents a hydrogen atom or an alkyl group, and X represents a chlorine, bromine or iodine atom or a cyano or $—SO_2R^5$ group where $R^5$ represents a hydrogen atom or an optionally substituted alkyl or aryl group. Compounds of general formula I exhibit biocidal activity.

10 Claims, No Drawings

PROCESS FOR THE PREPARATION OF AZOXYCYANIDE COMPOUNDS

This is a file wrapper continuation of application Ser. No. 08/291,268 filed on Aug. 16, 1994, now abandoned.

This invention relates to a process for the preparation of certain azoxycyanide compounds, especially arylazoxycyanide compounds which exhibit biocidal activity.

A number of routes for the preparation of arylazoxycyanide compounds have already been disclosed. For instance, Eur. J. Med. Chem.—Chim. Ther., 1982, 17, pp. 482–484 discloses the oxidation of an arylazocyanide under harsh conditions using 90% hydrogen peroxide in trifluoroacetic acid. However, such a route would be hazardous and expensive for the large scale preparation of arylazoxycyanide compounds.

European patent application no. 92120580.3 discloses a modification of the above oxidation process in which an arylazocyanide is oxidised under milder conditions with a mixture comprising hydrogen peroxide and methanoic acid and/or with peroxymethanoic acid. However, as this modified process still uses potentially hazardous materials, it is not suitable for use on a commercial scale.

Another route, described in J. Chem. Soc., Chem. Commun., 1984, pp 323–324, involves the reduction of an aromatic nitro group to a hydroxylamine followed by oxidation back to a nitroso compound and, in turn, coupling with cyanamide using iodobenzene diacetate in stoichiometric amounts. A severe disadvantage of this route for large scale preparation of arylazoxycyanide compounds is the requirement for stoichiometric amounts of iodobenzene diacetate. Iodobenzene diacetate is not available in large quantities and this adds significantly to the costs of the preparation.

A modification of the above process is described in European patent application no. 92120580.3 which uses dibromoisocyanuric acid in place of iodobenzene diacetate. However, although dibromoisocyanuric acid is cheaper to produce than iodobenzene diacetate, it is not commercially available. Moreover, in large scale preparation, dibromoisocyanuric acid causes the release of elemental bromine which partially oxidises the nitroso precursor to nitroaromatic compounds and the final product is therefore always contaminated with differing amounts of nitro compounds.

It has now been discovered that arylazoxycyanide compounds can be produced in high yield from the corresponding nitroso compound using reagents that are commercially available at reasonable prices. Moreover, since these reagents do not appear to cause the release of elemental bromine, the formation of undesired by-products is greatly reduced.

According to the present invention there is therefore provided a process for the preparaton of a compound of the general formula

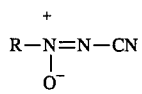
(I)

in which R represents an optionally substituted aryl or heterocyclyl group, which comprises treating a compound of the general formula

R—N=O (II)

in which R is as defined above, with cyanamide or a metal salt thereof and a compound of the general formula

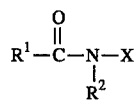
(III)

in which $R^1$ represents an optionally substituted alkyl or aryl group and $R^2$ represents a hydrogen atom or an optionally substituted alkyl or aryl group or $R^1$ and $R^2$ together represent a group

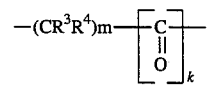

where m is 2, 3, 4 or 5, k is 0 or 1 and each of $R^3$ and $R^4$ independently represents a hydrogen atom or an alkyl group, and X represents a chlorine, bromine or iodine atom or a cyano or —$SO_2R^5$ group where $R^5$ represents a hydrogen atom or an optionally substituted alkyl or aryl group.

It should be noted that compounds of general formula I could be in any of the following isoelectronic forms:

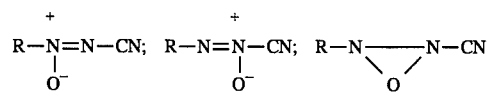

and the scope of the present invention covers all such forms.

Unless otherwise stated, when any of the compounds mentioned contain an alkyl, alkenyl or alkynyl substituent group, this may be linear or branched and may contain up to 12, preferably up to 6 and especially up to 4, carbon atoms. Cycloalkyl or cycloalkenyl groups may contain 3 to 8, preferably 3 to 6, carbon atoms. An aryl group may be any aromatic hydrocarbon group, especially a phenyl or naphthyl group. An aralkyl group comprises an alkyl group, as defined above, substituted by an aryl group, as defined above. A particularly preferred example of an aralkyl group is a benzyl group. A heterocyclyl group may be any saturated or unsaturated ring system containing at least one heteroatom, 3- to 6-membered rings being preferred and 5- and 6-membered rings being especially preferred. Nitrogen-, oxygen- and sulphur-containing heterocyclic rings, such as pyridyl, pyrimidinyl, pyrrolidinyl, furyl, pyranyl, morpholinyl and thienyl, are particularly preferred.

When any of the foregoing substituents are designated as being optionally substituted, the substituent groups which are optionally present may be any one or more of those customarily employed in the development of pesticidal compounds, and/or the modification of such compounds to influence their structure/activity, persistence, penetration or other property. Specific examples of such substituents include for example, halogen atoms, nitro, cyano, hydroxyl, alkyl, haloalkyl, alkoxy, haloalkoxy, amino, alkylamno, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms. Typically, 0–3 substituents may be present, most commonly 0 or 1.

The process described herein may be particularly, although not exclusively, of use in the preparation of the following groups of compounds.

In one group of compounds of interest, R represents a substituted phenyl group in which at least one substituent thereof is a group of general formula —NR⁶COR⁷ where R⁶ represents a hydrogen atom or an alkyl group and R⁷ represents a hydrogen atom or an optionally substituted alkyl, alkoxy, alkenyl, alkenyloxy, phenyl or phenoxy group. Preferably, R⁶ represents a hydrogen atom. Preferably, R⁷ represents a hydrogen atom or an optionally substituted alkyl, alkenyl, phenyl or alkoxy group. Preferably R⁷ represents a hydrogen atom, or an alkyl, haloalkyl (especially CF₃), alkoxy or phenyl group. Most preferably, a group —NR⁶COR⁷ is of formula —NHCOC₆H₅. Preferably, the phenyl group R carries only one substituent, preferably in the 2- or 4-position.

In another group of compounds of interest, R represents a substituted phenyl group in which at least one substituent thereof is an amido group, preferably of general formula —CONR⁸R⁹ where each of R⁸ and R⁹ independently represents a hydrogen atom or an optionally substituted (preferably unsubstituted) alkyl group, or an optionally substituted phenyl group, preferably phenyl optionally substituted by one or more halogen atoms(s) and/or alkyl group(s). Preferably, each of R⁸ and R⁹ independently represents a hydrogen atom, a C₁₋₄ alkyl group, or an optionally halosubstituted phenyl group. Preferably, at least one of R⁸ and R⁹ represents a hydrogen atom, and the other of R⁸ and R⁹ represents a hydrogen atom, methyl group, phenyl group or halophenyl group. Preferably, the phenyl group R carries only one substituent, preferably in the 2- or, more preferably, the 4-position.

In another group of compounds of interest, R may represent a group of general formula.

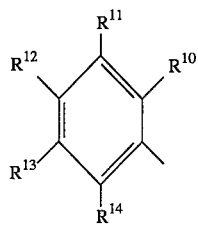
(IV)

where R¹⁰ and R¹¹ together, or R¹¹ and R¹² together, represent an optionally substituted hydrocarbyloxy chain and the ring is optionally substituted at any or each of the remaining sites R¹³, R¹⁴ and R¹⁰ or R¹².

The term "hydrocarbyloxy chain" is used herein to denote a carbon chain interrupted within the chain by one or more (but preferably one only) oxygen atom. A (or the) oxygen atom is preferably located at one end of the chain.

Optional substituent(s) of the hydrocarbyloxy chain are, suitably, optionally substituted alkyl group(s), preferably alkyl group(s) optionally substituted by one or more (preferably one) halogen atom(s) or hydroxy or alkoxy group(s); optionally substituted phenyl group(s); an alkylene group, preferably —(CH₂)₄—, across adjacent carbon atoms of the hydrocarbyloxy chain; or group(s) =O.

Preferably, the hydrocarbyloxy chain is unsubstituted or substituted by 1–2 alkyl, haloalkyl, hydroxyalkyl or alkoxyalkyl groups, or by one alkylene group —(CH₂)₄— alkoxyalkyl groups, or by one alkylene group —(CH₂)₄— across adjacent carbon atoms, or by a group =O.

A hydrocarbyloxy chain preferably has 3 or 4 chain atoms. Preferred hydrocarbyloxy chains may be represented by oxyalkylene and oxyalkenylene chains. Within the ambit of the term "oxyalkenylene" as used herein are chains in which the pi electrons form part of a resonance electron system. When the chain is oxyalkenylene the chain may form, with the phenyl ring, a fused heteroaromatic ring system.

Preferred oxyalkylene and oxyalkenylene chains are based upon these structures (side (atoms/groups not shown):

—O—C—C— (cf dihydrobenzo[b]furans)

—O—C=C (cf benzo[b]furans)

—O—C—C—C—

—O—C—C=C—

Particularly preferred oxyalkylene or oxyalkenylene chains are:

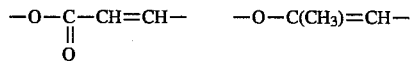

Optional substituents R¹³, R¹⁴ and R¹⁰ or R¹² are preferably selected from halogen atoms and alkyl and alkoxycarbonyl groups, especially chlorine, methyl and methoxycarbonyl. Most preferably, the sites R¹³, R¹⁴ and R¹⁰ or R¹² are all unsubstituted, or only one such site is substituted.

In another group of compounds of interest, R may represent a group of general formula

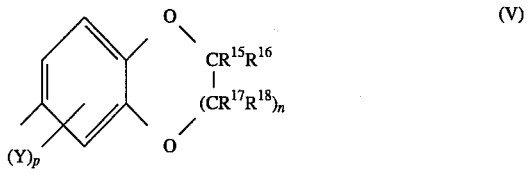
(V)

wherein n is 0 or 1; each of R¹⁵ and R¹⁶, and R¹⁷ and R¹⁸ if present, independently represents a hydrogen or halogen atom or an optionally substituted alkyl, cycloalkyl or aryl group, or R¹⁵ and R¹⁶ together or R¹⁷ and R¹⁸ together represent an optionally substituted alkylene chain; Y represents an alkyl group or a halogen atom; and p represents 0, 1, 2 or 3. Preferably each of R¹⁵ and R¹⁶ independently represents a hydrogen atom or a C₁₋₆ alkyl, C₃₋₆ cycloalkyl, phenyl or naphthyl group or R¹⁵ and R¹⁶ together represent a C₄₋₆ alkylene chain, each group or chain being optionally substituted by one or more substituents selected from halogen atoms, nitro, cyano, hydroxyl, C₁₋₄ alkyl, C₁₋₄ haloalkyl, C₁₋₄ alkoxy, C₁₋₄ haloalkoxy, C₁₋₄ alkylamino, di-C₁₋₄ alkylamino, C₁₋₄ alkoxycarbonyl and benzyloxycarbonyl groups. Preferably each of R¹⁷ and R¹⁸, if present, represents a hydrogen atom or a C₁₋₆ alkyl, C₃₋₆ cycloalkyl phenyl or naphthyl group or R¹⁷ and R¹⁸ together represent a C₄₋₆ alkylene chain, each group or chain being optionally substituted by one or more substituents selected from halogen atoms, nitro, cyano, hydroxyl, C₁₋₄ alkyl, C₁₋₄ haloalkyl, C₁₋₄ alkoxy, C₁₋₄ haloalkoxy, C₁₋₄ alkylamino, di-C₁₋₄ alkylamino, C₁₋₄ alkoxycarbonyl and benzyloxycarbonyl groups. Preferably, Y represents a fluorine or chlorine atom. Preferably p represents 0.

In another group of compounds of interest, R may represent a substituted phenyl group in which at least one substituent thereof is a group of general formula —S(O)$_q$Z wherein q represents 0, 1 or 2 and Z represents a hydrogen atom or an optionally substituted alkyl, cycloalkyl, aryl, aralkyl or amino group. More specficially, Z preferably represents an optionally substituted alkyl, cycloalkyl, aralkyl or aminio group. More preferably, Z represents a C₁₋₄ alkyl group, a C₃₋₆ cycloalkyl group, a benzyl group or a group of general formula NR²⁹R³⁰ where each of R²⁹ and R³⁰ independently represents a hydrogen atom, or an optionally substituted phenyl or alkyl group, or together may represent an alkylene chain which is optionally interrupted by an oxygen atom. Preferably, $R^{29}$ represents a hydrogen atom and $R^{30}$ represents a hydrogen atom, or a phenyl or halophenyl group, or an alkyl group optionally substituted by a group of general formula —$CO_2R^{31}$ where $R^{31}$ represents a hydrogen atom or an alkyl group; or $R^{29}$ and $R^{30}$ together represent a group of formula —$(CH_2)_2$—O—$(CH_2)_2$— (the group Z thus being an N-morpholino group). Preferably, the phenyl group R is substituted by one or more further substituents for example halogen atoms(s). Preferably, R represents a group of general formula

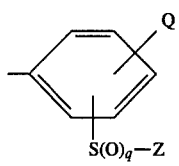

where Q represents a halogen, especially chlorine, atom, or most preferably, a hydrogen atom.

In another group of compounds of interest, R represents a group of general formula

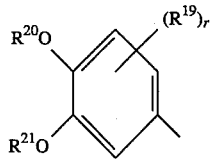

in which r is 0, 1, 2 or 3; each $R^{19}$ independently represents a halogen atom, nitro, cyano, alkyl, haloalkyl, alkoxy or haloalkoxy group; and each of $R^{20}$ and $R^{21}$ independently represents an optionally subsituted alkyl, alkenyl, alkynyl, cycloalkyl or aralkyl group. Preferably, each $R^{19}$ independently represents a halogen (especially fluorine or chlorine) atom, nitro, cyano, $C_{1-6}$ alkyl (especially methyl), $C_{1-6}$ haloalkyl (especially trifluoromethyl), $C_{1-6}$ alkoxy or $C_{1-6}$ haloalkoxy group. It is preferred that r is 0 or 1 and especially preferred that r is 0. Preferably, each of $R^{20}$ and $R^{21}$ independently represents a $C_{1-8}$ alkyl, $C_{2-6}$ alkenyl, $C_{2-6}$ alkynyl, $C_{3-8}$ cycloalkyl or benzyl group, each group being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino and $C_{1-4}$ alkoxycarbonyl groups.

In another group of compounds of interest, R represents a group of general formula

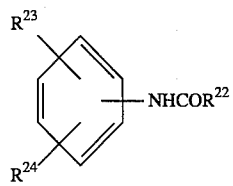

in which $R^{22}$ represents an optionally substituted alkyl, alkenyl, alkynyl, cycloalkyl, cycloalkenyl aryl or heterocyclyl group; $R^{23}$ represents a halogen atom, nitro, cyano or optionally subsituted alkyl, alkoxy, aryl or aryloxy group; and $R^{24}$ represents a hydrogen or halogen atom, nitro, cyano or optionally substituted alkyl or alkoxy group. Preferably, $R^{22}$ represents a $C_{1-6}$ alkyl, $C_{2-6}$ alkenyl, $C_{2-6}$ alkynyl, $C_{3-8}$ cycloalkenyl or phenyl group or 3- to 6-membered heterocyclic ring (especially an oxygen-containing ring), each group or ring being optionally substituted by one or more substituents selected from halogen (especially fluorine and chlorine) atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, $C_{1-4}$ alkoxycarbonyl and $C_{3-8}$ cycloalkyl groups. It is preferred that $R^{23}$ represents a halogen (especially chlorine) atom, a nitro or cyano group, or a $C_{1-6}$ alkyl (especially methyl) or $C_{1-6}$ alkoxy (especially methoxy) group each optionally substituted (but preferably unsubstituted) by one or more substituents selected from halogen (especially fluorine or chlorine) atoms, nitro, cyano, hydroxyl and amino groups. It is also preferred that $R^{24}$ represents a hydrogen or halogen (especially chlorine) atom. Preferably, the group —$NHCOR^{22}$ is attached to the 3- or, especially, 4-position of the benzene ring in the azoxycyanobenzene moiety.

In another group of compounds of interest, R represents a group of general formula

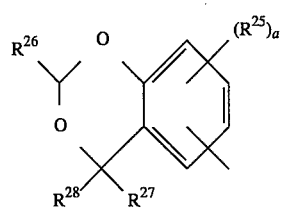

in which s is 0, 1 or 2; each $R^{25}$, if present, independently represents a halogen atom or an optionally substituted alkyl or alkoxy group; $R^{26}$ represents a hydrogen atom or a haloalkyl group; and $R^{27}$ and $R^{28}$ independently represent a hydrogen atom or an alkyl or haloalkyl group. Preferably, s is 0 or 1 and each $R^{25}$, if present, represents a halogen (especially chlorine or bromine) atom or a $C_{1-6}$ alkyl (especially methyl) or $C_{1-6}$ alkoxy (especially methoxy) group, each group being optionally substituted by one or more substituents selected from halogen atoms, nitro, cyano, hydroxyl and amino groups. It is preferred that $R^{26}$ represents a hydrogen atom or a $C_{1-6}$ haloalkyl group, the or each halogen atom in the haloalkyl group preferably being a fluorine or chlorine atom. It is also preferred that $R^{27}$ and $R^{28}$ independently represent a hydrogen atom or a $C_{1-6}$ alkyl or $C_{1-6}$ haloalkyl group, the or each halogen atom in the haloalkyl group preferably being a fluorine or chlorine atom. Preferably, the azoxycyano group is located at the 5-, 6- or 7-position of the 1,3-benzodioxane ring, the 6-position being especially preferred.

If a metal salt of cyanamide is used in the process of the invention, it is preferred that the metal salt is an alkali metal salt or an alkaline earth metal salt. Alternatively, such metal salts can be generated in situ By reacting cyanamide with an alkali metal hydroxide or an alkaline earth metal hydroxide. The use of monosodium cyanamide is especially preferred. Alternatively, this may be replaced by a concentrated aqueous solution of cyanamide with sodium hydroxide which effectively generates monosodium cyanamide in situ.

The compound of formula III may be a cyclic or linear N-halogen or pseudohalogen amide or imide. In the case of linear compounds, it is preferred that $R^1$ represents a $C_{1-6}$ alkyl, particularly a $C_{1-4}$ alkyl and especially a methyl, group and $R^2$ represents a hydrogen atom. In the case of cyclic compounds, it is preferred that $R^1$ and $R^2$ together represent a group

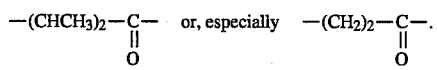

It is also preferred that X represents an iodine or, especially, a chlorine or bromine atom. If X represents a group $-SO_2R^5$, it is preferred that $R^5$ represents a $C_{1-4}$ alkyl, especially a methyl, group or a tolyl group. Particularly preferred compounds of formula III are N-chlorosuccinimide and, especially, N-bromosuccinimide.

The process is preferably carried out at a temperature in the range from $-5°$ C., to $35°$ C., a temperature in the range from $0°$ C. to ambient temperature (about $20°$ C.) being especially preferred.

The reaction may be conveniently carried out in the presence of a solvent. Suitable solvents include dimethylformamide and chlorinated hydrocarbons such as dichloromethane.

If monosodium cyanamide (or a generator thereof) and N-bromosuccinimide are used, the N-bromosuccinimide should be added to the nitroso compound of formula II before the addition of the monosodium cyanamide to avoid the production of undesired adducts between the cyanamide and the nitroso compound.

Compounds of formula II may be prepared according to the process of R. J. W. LeFevre and H. Vine, J. Chem. Soc., 1938, 431. Compounds of formula III are known compounds or may be prepared by processes analogous to known processes.

The invention also extends to compounds of general formula I whenever prepared by a process as described herein.

Certain compounds of general formula I exhibit biocidal, especially fungicidal, activity. Many of the compounds exhibit particularly good activity against phytopathogenic fungi.

The invention is further illustrated by the following examples.

EXAMPLE 1

Preparation of
[4-(N-phenylamido)phenyl]-ONN-azoxycyanide
(R=4-CONHC$_6$H$_5$ phenyl)

4-(N-phenylamido)nitrosobenzene (2.7 g, 11.9 mmol) was suspended in dimethylformamide (65 ml). N-bromosuccinimide (2.17 g, 12.2 mmol) was added at once. The reaction mixture was treated in portions with monosodium cyanamide (1.18 g, 18.4 mmol). After 30 minutes at ambient temperature, the mixture was poured on water (700 ml) and the yellow solid filtered, washed with water and dried to give 2.41 g [4-(N-phenylamido)phenyl]-ONN-azoxycyanide as yellow crystals, m.pt. 220°–225° C. (Yield: 76.0% of theoretical).

EXAMPLE 2

Preparation of
[4-phenylamido)phenyl]-ONN-azoxycyanide
(R=4-CONHC$_6$H$_5$ phenyl)

4-(N-phenylamido)nitrosobenzene (5.0 g, 22.1 mmol) was suspended in dimethylformamide (50 ml) and N-bromosuccinimide (5.9 g, 33.2 mmol) was added at once. At ambient temperature, the reaction mixture was treated drop by drop with a solution of monosodium cyanamide (2.1 g, 32.8 mmol) in water (4 ml). After 20 minutes, the mixture as poured on ice-water (200 ml). The resulting yellow solid was filtered, washed with water and air dried to give 5.3 g [4-(N-phenylamido)phenyl]-ONN-azoxycyanide as a yellow powder, m.pt. 220°–225° C. (Yield: 90.1% of theoretical).

EXAMPLE 3

Preparation of
[4-(N-phenylamido)phenyl]-ONN-azoxycyanide
(R=4-CONHC$_6$H$_5$phenyl)

4-(N-phenylamido)nitrosobenzene (2.0 g, 8.8 mmol) was suspended in dimethylformamide (20 ml) and N-bromosuccinimide (2.4 g, 13.5 mmol) was added. At 20°–25° C. a solution of cyanamide (0.56 g, 13.3 mmol) and sodium hydroxide (0.51 g, 12.8 mmol) in water (3 ml) was added drop by drop over a period of 10 minutes. After 1 hour, the suspension was poured on ice-water (100 ml). The resulting solid was filtered, washed with water and dried to give 2.1 g [4-(N-phenylamido)phenyl]-ONN-azoxycyanide as a yellow powder, m.pt. 220°–225° C. (Yield: 89.6% of theoretical).

EXAMPLE 4

Preparation of
4-(N-acetylamino)phenyl-ONN-azoxycyanide
(R=4-NHCOCH$_3$ phenyl)

4-(N-acetylamino)nitrosobenzene (15.0 g, 91.5 mmol) and N-bromosuccinimide (16.3, 91.6 mmol) were dissolved in dimethylformamide (150 ml). At ambient temperature, the solution was treated with monosodium cyanamide (9.14 g, 142.8 mmol). After 45 minutes, the brown solution was treated with N-bromosuccinimide (6.4 g, 36 mmol) and stirred for an additional 1½ hours. The mixture was poured on ice-water (500 ml) and left overnight. The yellow crystallised precipitate was collected and dried to give 16.8 g 4-(N-acetylamino)phenyl-ONN-azoxycyanide as a yellow powder, m.pt. 240°–242° C. (Yield: 90% of theoretical).

EXAMPLE 5

Preparation of
(4-N-acetylamino)phenyl-ONN-azoxycyanide
(R=4-NHCOCH$_3$phenyl)

4-(N-acetylamino)nitrosobenzene (1.64 g, 10.0 mmol) was dissolved in dimethylformamide (20 ml) and treated with monosodium cyanamide (1.0 g, 15.6 mmol). N-chlorosuccinimide (1.33 g, 10.0 mmol) was added and the mixture stirred for 24 hours at ambient temperature. The mixture was poured on ice-water (100 ml) and the precipitate filtered off to give 1.2 g 4-(N-acetylamino)phenyl ONN-azoxycyanide as a yellow powder, m.pt. 240°–242° C. (Yield: 58.8% of theoretical).

EXAMPLE 6

Preparation of
1,3-benzodioxanyl-6-ONN-azoxycyanide
(R=1,3-benzodioxan-6-yl)

6-Nitroso-1,3-benzodioxane (1.0 g, 6.1 mmol) and N-bromosuccinimide (1.1 g, 6.2 mmol) were dissolved in dimethylformamide (20 ml). Monosodium cyanamide (0.61 g, 9.5 mmol) was added. The mixture was stirred for 1 hour at ambient temperature and poured on ice-water (80 ml), filtered, washed with water and dried to give 0.9 g 1,3-benzodioxanyl-6-ONN-azoxycyanide as a yellow powder, m.pt. 156°–158° C. (Yield: 71.9% of theoretical).

EXAMPLE 7

Preparation of 3,4-methylenedioxyphenyl-ONN-azoxycyanide (R=3,4-OCH$_2$O-phenyl).

3,4-Methylenedioxynitrosobenzene (1.05 g, 6.9 mmol) was dissolved in dichloromethane (20 ml). After the addition of cyanamide (0.42 g, 9.9 mmol) and N-bromosuccinimide (1.8 g, 9.9 mmol) the mixture was stirred at ambient temperature overnight. The resulting mixture was filtered and evaporated to dryness. Column chromatography on silica using 1:1 petroleum ether: ethyl acetate as eluant yielded 1.1 g 3,4-methylenedioxyphenyl-ONN-azoxycyanide as a yellow solid, m.pt. 145°–147° C. (Yield: 82.7% of theoretical).

I claim:

1. A process for the preparation of a compound of the general formula $$R-\underset{O^-}{\overset{+}{N}}=N-CN \qquad (I)$$

in which R represents an optionally substituted aryl or heterocyclyl group, which comprises treating a compound of the general formula $$R-N=O \qquad (II)$$

in which R is as defined above, with cyanamide or a metal salt thereof and a compound of the general formula $$R^1-\underset{R^2}{\overset{O}{\overset{\|}{C}}}-N-X \qquad (III)$$

in which R$^1$ represents an optionally substituted alkyl or aryl group and R$^2$ represents a hydrogen atom or an optionally substituted alkyl or aryl group or R$^1$ and R$^2$ together represent a group $$-(CR^3R^4)m-\left[\underset{O}{\overset{\|}{C}}\right]_k-$$

where m is 2, 3, 4 or 5, k is 0 or 1 and each of R$^3$ and R$^4$ independently represents a hydrogen atom or an alkyl group, and X represents a chlorine, bromine or iodine atom or a cyano or —SO$_2$R$^5$ group where R$^5$ represents a hydrogen atom or an optionally substituted alkyl or aryl group.

2. A process according to claim 1 in which R represents a substituted phenyl group in which at least one substituent thereof is a group of general formula —NR$^6$COR$^7$ where R$^6$ represents a hydrogen atom or an alkyl group and R$^7$ represents a hydrogen atom or an optionally substituted alkyl, alkoxy, alkenyl, alkenyloxy, phenyl or phenoxy group.

3. A process according to claim 1 in which R represents a substituted phenyl group in which at least one substituent thereof is an amido group of general formula —CONR$^8$R$^9$ where each of R$^8$ and R$^9$ independently represents a hydrogen atom or an optionally substituted alkyl or phenyl group.

4. A process according to claim 1 in which R represents a group of general formula <chemical structure (IV) with substituents R$^{10}$, R$^{11}$, R$^{12}$, R$^{13}$, R$^{14}$ on a phenyl ring> in which R$^{10}$ and R$^{11}$ together, or R$^{11}$ and R$^{12}$ together, represent an optionally substituted hydrocarbyloxy chain and the ring is optionally substituted at any or each of the remaining sites R$^{13}$, R$^{14}$ and R$^{10}$ or R$^{12}$.

5. A process according to claim 1 in which R represents a group of general formula <chemical structure (V) showing a phenyl ring with a fused dioxy ring containing CR$^{15}$R$^{16}$ and (CR$^{17}$R$^{18}$)$_n$, with (Y)$_p$ substituents> in which n is 0 or 1; each of R$^{15}$ and R$^{16}$, and R$^{17}$ and R$^{18}$ if present, independently represents a hydrogen or halogen atom or an optionally substituted alkyl, cycloalkyl or aryl group, or R$^{15}$ and R$^{16}$ together or R$^{17}$ and R$^{18}$ together represent an optionally substituted alkylene chain; Y represents an alkyl group or a halogen atom; and p represents 0, 1, 2 or 3.

6. A process according to claim 1 in which R represents a substituted phenyl group in which at least one substituent thereof is a group of general formula —S(O)$_q$Z where q represents 0, 1 or 2 and Z represents a hydrogen atom or an optionally substituted alkyl, cycloalkyl, aryl, aralkyl or amino group.

7. A process according to claim 1 in which R represents a group of general formula <chemical structure (VI) with R$^{20}$O, R$^{21}$O, and (R$^{19}$)$_r$ substituents on a phenyl ring> in which r is 0, 1, 2 or 3; each R$^{19}$ independently represents a halogen atom, nitro, cyano, alkyl, haloalkyl, alkoxy or haloalkoxy group; and each of R$^{20}$ and R$^{21}$ independently represents an optionally substituted alkyl, alkenyl, alkynyl, cycloalkyl or aralkyl group.

8. A process according to claim 1 in which R represents a group of general formula

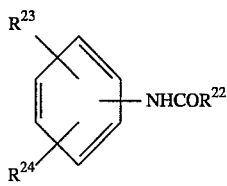 (VII)

in which $R^{22}$ represents an optionally substituted alkyl, alkenyl, alkynyl, cycloalkyl, cycloalkenyl, aryl or heterocyclyl group; $R^{23}$ represents a halogen atom, nitro, cyano or optionally substituted alkyl, alkoxy, aryl or aryloxy group; and $R^{24}$ represents a hydrogen or halogen atom, nitro, cyano or optionally substituted alkyl or alkoxy group.

9. A process according to claim 1 in which R represents a group of general formula

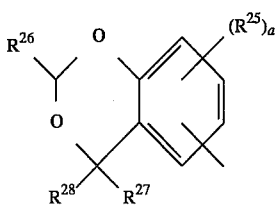 (VIII)

in which s is 0, 1 or 2; each $R^{25}$, if present independently represents a halogen atom or an optionally substituted alkyl or alkoxy group; $R^{26}$ represents a hydrogen atom or a haloalkyl group; and $R^{27}$ and $R^{28}$ independently represent a hydrogen atom or an alkyl or haloalkyl group.

10. A process according to claim 1 in which the compound of formula III is N-bromosuccinimide.

* * * * *